United States Patent
Burckard

(10) Patent No.: US 9,830,472 B2
(45) Date of Patent: Nov. 28, 2017

(54) METHOD FOR HANDLING PRIVACY DATA

(75) Inventor: Antoine Burckard, Montigny le Bretonneux (FR)

(73) Assignee: NAGRAVISION S.A., Cheseaux-sur-Lausanne (CH)

( * ) Notice: Subject to any disclaimer, the term of this patent is extended or adjusted under 35 U.S.C. 154(b) by 0 days.

(21) Appl. No.: 14/114,873

(22) PCT Filed: May 9, 2012

(86) PCT No.: PCT/EP2012/058580
§ 371 (c)(1),
(2), (4) Date: Oct. 30, 2013

(87) PCT Pub. No.: WO2012/152845
PCT Pub. Date: Nov. 15, 2012

(65) Prior Publication Data
US 2014/0068257 A1    Mar. 6, 2014

Related U.S. Application Data

(60) Provisional application No. 61/484,266, filed on May 10, 2011.

(30) Foreign Application Priority Data

May 10, 2011    (EP) .................................... 11165570

(51) Int. Cl.
*H04L 29/06*    (2006.01)
*G06F 21/62*    (2013.01)
(Continued)

(52) U.S. Cl.
CPC .......... *G06F 21/6245* (2013.01); *G06F 21/10* (2013.01); *G06F 21/6218* (2013.01);
(Continued)

(58) Field of Classification Search
CPC .. G06F 21/6245; G06F 21/10; G06F 21/6218; G06F 1/6218; G06F 1/10; H04L 63/0435; G06Q 50/24; G06Q 50/06
(Continued)

(56) References Cited

U.S. PATENT DOCUMENTS 6,023,765 A     2/2000  Kuhn
6,363,481 B1 *  3/2002  Hardjono ................ H04L 9/085
                                                         713/165
(Continued)

FOREIGN PATENT DOCUMENTS

CN     1531820     9/2004
CN     101061484   10/2007
(Continued)

OTHER PUBLICATIONS

International Search Report issued in International Application No. PCT/EP2012/058580, dated Aug. 3, 2012.
(Continued)

*Primary Examiner* — Shewaye Gelagay
*Assistant Examiner* — Amie C Lin
(74) *Attorney, Agent, or Firm* — DLA Piper LLP (US)

(57) ABSTRACT

The present invention aims to improve data protection against illegal access by a strong differentiation of the security level specific on a type of data so that when the protection on a part of the data is violated, the remaining data are still inaccessible. A method for controlling access, via an open communication network, to user private data, comprising steps of: dividing the user private data into a plurality of categories, each category defining a privacy level of the data, encrypting the user private data of each category with a category key pertaining to the category of the data, attributing to a stakeholder a device configured for accessing to at least one category of user private data, and
(Continued)

authorizing the access to the at least one category of user private data for the device of the stakeholder, by providing the stakeholder with the category keys required for decrypting the user private data of the corresponding category.

15 Claims, 2 Drawing Sheets

(51) Int. Cl.
  *G06Q 50/24* (2012.01)
  *G06F 21/10* (2013.01)
  *G06Q 50/06* (2012.01)

(52) U.S. Cl.
  CPC ............ *G06Q 50/06* (2013.01); *G06Q 50/24* (2013.01); *H04L 63/0435* (2013.01)

(58) Field of Classification Search
  USPC ........................................................ 713/166
  See application file for complete search history.

(56) References Cited

U.S. PATENT DOCUMENTS

| | | | |
|---|---|---|---|
| 6,463,417 B1* | 10/2002 | Schoenberg | G06F 19/322 705/2 |
| 7,827,234 B2 | 11/2010 | Eisenberger et al. | |
| 7,921,284 B1 | 4/2011 | Kinghorn et al. | |
| 7,949,619 B2 | 5/2011 | Narayanaswamy et al. | |
| 2003/0002668 A1 | 1/2003 | Graunke et al. | |
| 2003/0051159 A1* | 3/2003 | McCown | H04N 7/1675 726/5 |
| 2004/0103202 A1 | 5/2004 | Hildebrand et al. | |
| 2005/0216313 A1 | 9/2005 | Claud et al. | |
| 2006/0143189 A1* | 6/2006 | Imaeda | G06F 21/335 |
| 2006/0155578 A1 | 7/2006 | Eisenberger et al. | |
| 2007/0195960 A1* | 8/2007 | Goldman et al. | 380/286 |
| 2008/0109285 A1* | 5/2008 | Reuther et al. | 705/7 |
| 2008/0256248 A1 | 10/2008 | Eisenberger et al. | |
| 2009/0326967 A1* | 12/2009 | Kaloboukis | G06Q 30/02 705/1.1 |
| 2010/0179831 A1* | 7/2010 | Brown | G06F 19/322 705/3 |
| 2010/0293045 A1 | 11/2010 | Burns et al. | |
| 2011/0258438 A1* | 10/2011 | Hildebrand | 713/165 |
| 2011/0296199 A1 | 12/2011 | Kinghorn et al. | |
| 2012/0078548 A1* | 3/2012 | Salazar et al. | 702/62 |
| 2013/0318347 A1* | 11/2013 | Moffat | H04L 63/08 713/168 |

FOREIGN PATENT DOCUMENTS

| | | |
|---|---|---|
| EP | 1 320 012 | 6/2003 |
| WO | WO 03/005175 | 1/2003 |
| WO | WO 03/049000 | 6/2003 |
| WO | WO 2006/072610 | 7/2006 |

OTHER PUBLICATIONS

Written Opinion issued in International Application No. PCT/EP2012/058580, dated Aug. 3, 2012.

Ravi S. Sandhu et al., "Access Control: Principles and Practice", IEEE Communications Magazine, vol. 32, No. 9, pp. 40-48, Sep. 1994.

Erman Ayday et al., "Secure, Intuitive and Low-Cost Device Authentication for Smart Grid Networks", The 8th Annual IEEE Consumer Communications and Networking Conference, pp. 1161-1165, Jan. 9, 2011.

Sameera Abdulrahman Almulla et al., "Cloud Computing Security Management", 2010 Second International Conference on Engineering Systems Management and Its Applications, pp. 1-7, Mar. 30, 2010.

Chinese Office Action issued in CN 201280022311.7 dated Jan. 26, 2016.

English language translation of Chinese Office Action issued in CN 201280022311.7 dated Jan. 26, 2016.

English language abstract of CN 101061484 published Oct. 24, 2007.

English language abstract of CN 1531820 published Sep. 22, 2004.

* cited by examiner

METHOD FOR HANDLING PRIVACY DATA

CROSS REFERENCE TO RELATED APPLICATIONS

This application is a U.S. National Stage Application of International Application No. PCT/EP2012/058580 filed May 9, 2012, which claims priority from U.S. Patent Application No. 61/484,266 filed May 10, 2011 and European Patent Application No. 11165570.0 filed May 10, 2011.

FIELD OF THE INVENTION

The present invention relates to user private data protection in a context of open or distributed networks, smart grids or cloud.

TECHNICAL BACKGROUND

As an increasing number and variety of devices are inter-connected via open or distributed networks, any information exchanged between the devices becomes potentially accessible to any one for any purpose. Certain type of information, in particular personal data of device users, subscribers or contributors require a specific protection through an efficient access control.

The usual solutions for protecting sensitive personal data are based on encryption at their transmission from a source device to a centralized storing device which nevertheless may be accessible to any third parties even to not concerned persons.

Document US2005/0216313A1, discloses an electronic medical record keeping system including a central data collection and data storage server linked via a network to different health data input sources. Each source provides controlled unidirectional input data via a first encryption key code for individual patients thereby enabling assimilation of data in the central server uniquely for each patient segregated from all other patient data. The sources further include a second encryption key code for the patient correlated with the first key code to enable initiation of a set of tool bar screens at a terminal accessed by the patient or doctor if authorized and bidirectional network connection to the unique patient data stored in the remote server.

Document WO2003/049000A1 discloses a method allowing users to store portions of their identity information with one or more identity providers. Identity information includes attributes such as the user's name, mailing address, e-mail, telephone number, and credit card number. An identity provider is an entity that creates, manages, and stores identity information for a plurality of users. A service provider is an entity that provides a service to a user and makes use of the aspects of the user's identity it has been authorized to access. A user can authenticate with an identity provider using, for example, a password-based credential or any other authentication mechanism. Service providers can then rely upon that authentication to provide access to authorized resources without requiring additional authentication. In some embodiments, however, additional authentication is performed because of the quality of the credential the user initially used to sign into the identity provider. Sensitive data have thus enhanced protection thanks to encryption and are accessible only to users having the necessary credential.

In this system user data are stored in several distributed databases having specific access controls requiring authentication either with an identity provider or a stronger authentication with signature.

Document U.S. Pat. No. 7,949,6191B1 discloses a method for managing customer data. This method includes assigning one or more roles with entities desiring access to customer data, the entities including at least one application. The method provides for determining a category associated with at least some of the customer data, determining an access level for each role based on the category associated with the at least some of the customer data, and restricting access by the application to a system maintaining the customer data based on whether the application is authorized to access the system.

In this document the mechanism of access levels to the customer data are defined as categories based on rules. The customer data are protected in a same way by an access control to a centralized database where all the customer data are stored. If a third party attempts to circumvent the rules, all data which is controlled by the rules in question may become accessible at a same time.

Document "Access Control: Principles and Practice", Ravi S. Sandhu and Pierangela Samarati, IEEE Communications Magazine discloses an access control coupled with an authentication of a user with a reference monitor linked with an authorization database. Objects are protected with access rights such as read only, read/write so that each user has its own access rights depending on the class of the object. An access matrix is thus defined with rights attributed to each user for accessing different files and accounts.

Document EP1320012A2 discloses a system and method for providing distributed access control. A number of local servers are employed to operate largely on behalf of a central server responsible for centralized access control management. Such a distributed fashion ensures the dependability, reliability and scalability of the access control management undertaking by the central server. According an embodiment, a distributed access control system that restricts access to secured items can include at least a central server having a server module that provides overall access control, and a plurality of local servers. Each local server can include a local module providing local access control. The access control, performed by the central server or the local servers, operates to permit or deny access requests to the secured items by requestors.

According to a further embodiment, a secured document includes a header and encrypted data portion. The header includes encrypted security information to control the access to the encrypted data portion. A user key associated with an authenticated user must be retrieved in order to decrypt the encrypted security information.

According to a further embodiment, a secured file or secured document includes two parts: an attachment, referred to as a header, and an encrypted document or data portion. The header includes security information that points to or includes the access rules and a file key. The access rules facilitate restrictive access to the secured document and essentially determine who/when/how/where the secured document can be accessed. The file key is used to encrypt/decrypt the encrypted data portion.

The method of EP1320012A2 appears thus to be rather complex with at least two levels of encryption: encryption of the security information in a header portion and encryption of the data portion with a key defined by the security information. Access rules are also used after decryption of the header.

SUMMARY OF THE INVENTION

An aim of the present invention is to improve data protection against illegal access by a strong differentiation of the security level specific on a type of data so that when the protection on a part of the data is violated, the remaining data are still inaccessible.

The aim is achieved by a method for controlling access, via an open communication network, to user private data provided by a plurality of digital data source devices, comprising steps of:

dividing the user private data into a plurality of categories, each category defining a privacy level of the user private data;

encrypting by each digital data source device the user private data of each category with a category key pertaining to the category of the user private data;

attributing to a stakeholder at least one client digital data processing device configured for accessing to at least one category of user private data, and authorizing the access to the at least one category of user private data for the at least one client digital data processing device of the stakeholder, by providing the at least one client digital data processing device with the category keys required for decrypting the user private data of the corresponding category.

An advantage of the method is that the data are not necessarily stored in a centralized database but they may be localized at a plurality of devices, nodes or local storage devices connected on the network. These distributed data are then organized in different categories related to the privacy level and encrypted accordingly. The access to the data by a device of a first stakeholder is thus rendered selective by the possession of the keys able to decrypt the category of data the first stakeholder is authorized to access. The other data categories remain inaccessible for this first device as they are each encrypted by different keys. A second device of a second stakeholder having a different set of keys can decrypt all or part of these categories which were forbidden for the first device.

A stakeholder is a generic term for designating an authorized person, a group or a company intervening in an open or distributed network where user private data are available. A telephony operator, an utility provider, a service provider, a health care provider, a physician, a banker, a lawyer, political authorities, a superior, parent, friend or other relative to a given person, etc. are examples of stakeholders which may have selective rights to access to private data of their related users, subscribers, customers, clients etc.

A device as defined herein may provide, process, store, manage, receive or access to digital data available in the open network.

An open or distributed communication network also called cloud is a concept consisting in transferring on distant servers data processing which is usually located on local servers or on a user client device. The cloud computing is a particular way of managing data as the location of the data is not known by the users or clients. The stakeholders are no more managers of their servers but they can access, in an evolutionary way, to numerous on-line services without managing a complex structure supporting these services. The applications and the data are not recorded in a local computer but in a cloud made up of a certain number of distant servers interconnected by means of high bandwidth communication channels necessary for efficient system fluidity. The access to the cloud is usually achieved by using web-based applications using for example an Internet browser.

The cloud computing is comparable to an electrical power distribution network. The information processing and storage capacity is proposed to the consumption by specialized providers or operators and invoiced according to the real using. Therefore, the stakeholders do no more require their own servers but subcontract this resource to a trusted company guaranteeing an on-demand processing and storage capacity. This notion is also known by the expression "elastic computing capacity" because cloud computing is a convenient on-demand model for establishing an access via the network to a shared configurable storage of information resources which are quickly available by minimizing managing efforts and contacts with the service provider.

The network where the method of the invention applies may also be a part or an entire smart grid as well as a part or an entire home area network.

A smart grid defines usually an intelligent electrical power distribution network using computer technologies for optimizing the production and the distribution and better link supply and demand between electricity providers and consumers. Furthermore the computer technologies aim to save energy, secure the network and reduce managing and operating costs. The smart grid concept is also associated to smart meters able to provide a time slot billing allowing consumers to choose the best rate among various electricity providers and to select hours of consumption allowing a better using of the electric network. Such a system may also allow mapping consumption more finely for anticipating future needs at more local scales.

A home area network or home network is a residential local area network (LAN). It allows communication between digital devices typically deployed in the home, usually a small number of personal computers and accessories, such as printers and mobile computing devices. An important function is the sharing of Internet access, often a broadband service through a cable TV or Digital Subscriber Line (DSL) provider. Additionally, a home server may be added for increased functionality. Home networks may use wired or wireless technologies using among others for example WiFi (IEEE 802.11) communication protocols.

In the document "Access Control: Principles and Practice", Ravi S. Sandhu and Pierangela Samarati, IEEE Communications Magazine no encryption of the data with a key specific to the category of the data is mentioned. The differentiation of the security level seems thus to be rather weak. In fact, if a read-only right on certain files is modified to a read-and-write right, other files having the same read-only right may be also modified. It means that the "granularity" for differentiating rights on files is quite low. A further aim of the present invention is also to increase this granularity by multiplying the number of categories and in parallel, the corresponding keys to decrypt the data according to their category.

Document EP1320012A2 does not mention steps of dividing user private data into a plurality of categories where each category defines a privacy level of the user private data and encrypting the user private data of each category with a category key pertaining to the category of the user private data.

The problem solved by the present invention is to improve in an efficient way the security of private user data with a strong differentiation of the security level for each category of data i.e. data sharing a common privacy level. The access to the data is controlled by attributing a specific set of category keys to concerned stakeholders. If a key is discovered, only one category of data is concerned without any security loss on other categories.

The present invention allows a high granularity of the protection thanks to the keys diversity. The data can be distributed in a large network (cloud) and be accessible from any location of the network in condition to dispose the appropriate category key. The security of storage location may also vary with the category.

BRIEF DESCRIPTION OF THE DRAWINGS

The invention will be better understood with the following detailed description, which refers to the attached figure given as a non-limitative example.

DETAILED DESCRIPTION OF THE INVENTION

Figure 1:
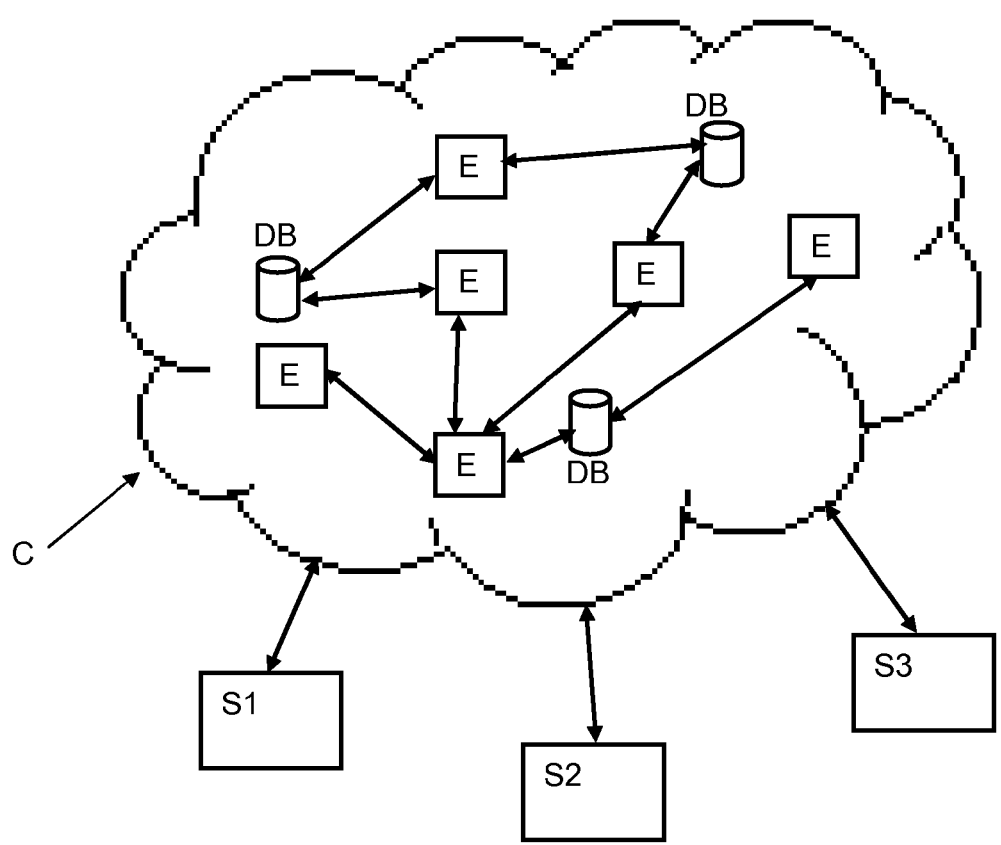
FIG. 1 shows a block diagram of an open network (cloud, smart grid, home area network, etc.) comprising data processing devices and storage devices providing user private data accessible by authorized stakeholders.

FIG. 1 illustrates an example of an open network C comprising a plurality of interconnected digital data processing devices E and databases DB controlled by the devices E. Stakeholders S1, S2, S3 have access to the data provided directly by the devices E or to data stored in the databases DB or a to datasets provided by both the devices E and the databases DB. The access to the data depends on authorizations given to the stakeholders S1, S2, S3 in form of keys allowing decrypting one or more categories of data.

Figure 2:
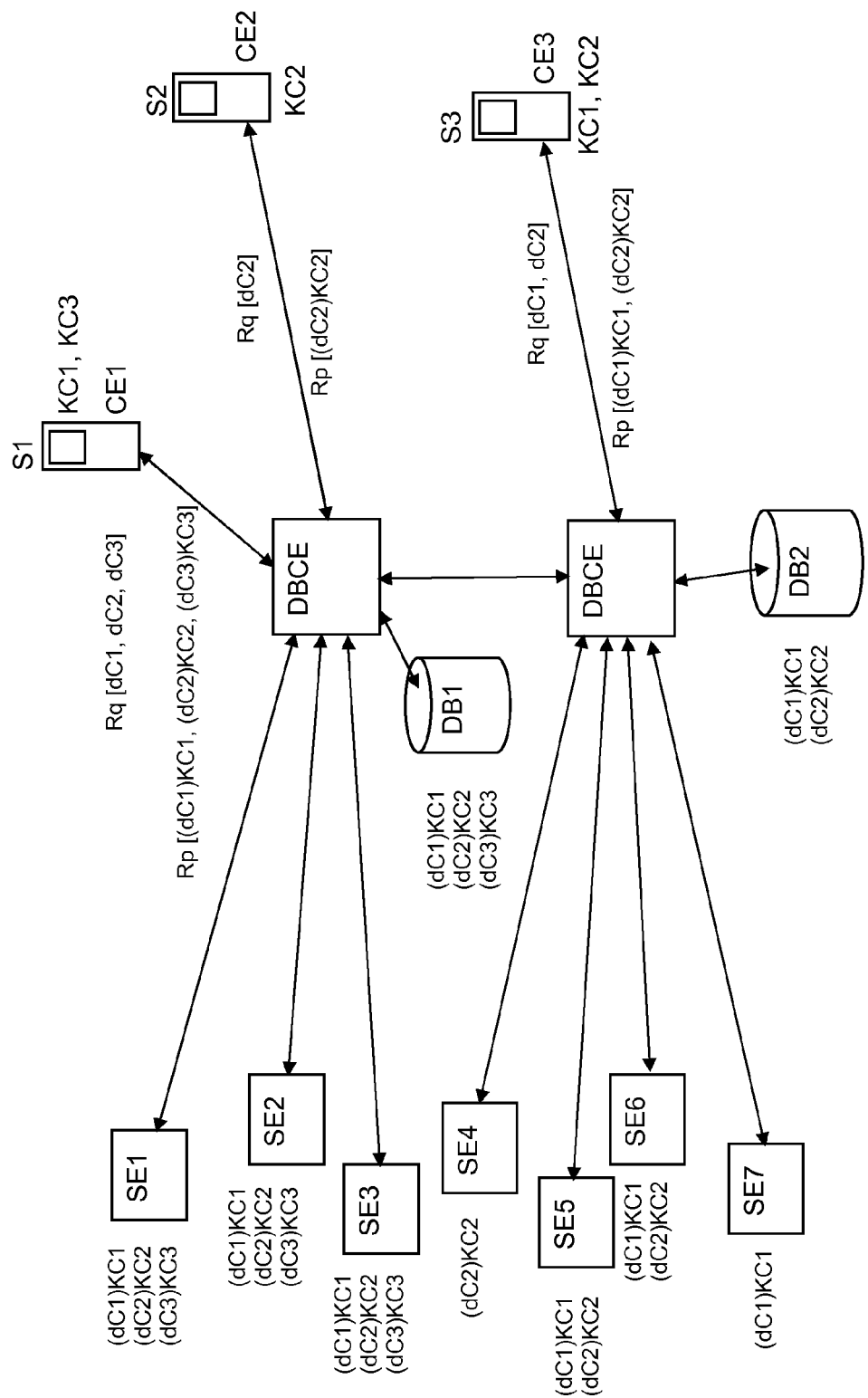
FIG. 2 shows an example of open network in which a plurality of categories of encrypted data are made available to stakeholders owning the appropriate keys for decrypting the data categories to which they are authorized to access.

An example of open network is detailed on FIG. 2 where digital data source devices SE1, SE2, SE3, SE4, SE5, SE6 and SE7 provide user private data (dC1, dC2, . . . dCn) of predetermined categories (C1, C2, . . . Cn). Each category of user private data (dC1, dC2, . . . dCn) is encrypted by the concerned digital data source device with a category key (KC1, KC2, . . . KCn).

In a smart grid context, these digital data source devices may for example consist of smart meters measuring values corresponding to energy, fluid, heat or multimedia communication data consumption. These values are divided into categories (C1, C2, . . . Cn) depending on their nature, service provider or privacy. For example electrical energy consumption does not concern the same provider or operator than the multimedia communication data. Furthermore a combination of a category of data with another one may have a certain privacy level requiring a particular protection.

According to other examples the digital data source devices (SE1, SE2, . . . SEn) may be electrical vehicles, or RFID devices or any device providing private data to be protected which are associated to one or several users.

Since user private data organized in categories relate to different users U1, U2, . . . Uk the category keys may be used in combination with other keys such as user-related keys. Categories and Users are orthogonal divisions of data. Category keys can be used at a dedicated layer of a key ladder.

In the example of FIG. 2 digital data source devices SE5, SE6 produce private data dC1 and dC2 of category C1 and C2 each encrypted with a respective category key KC1 and KC2.

Digital data source devices SE1, SE2 and SE3 produce data dC1, dC2 and dC3 of category C1, C2 and C3 each encrypted with their respective category key KC1, KC2 and KC3.

Digital data source device SE4 produces data dC2 of category C2 encrypted with its respective category key KC2.

Digital data source device SE7 produces data dC1 of category C1 encrypted with its respective category key KC1.

The category keys (KC1, KC2, . . . KCn) are either of symmetrical type or asymmetrical type or of a combination of symmetrical and asymmetrical keys. In a configuration example, public keys are stored in the digital data source devices while the corresponding private keys are stored in the devices controlled by the stakeholders entitled to access data dC1, dC2 and dC3.

Database controllers DBCE or managing centers, process, manage, sort the produced data which may be temporarily or permanently stored into databases DB. In the example, user data such as identifier, name, address, smart meter identifier, type, location etc. are stored in the databases together with smart meter value data gathered by the database controllers DBCE. These user data considered as of a high privacy level are of categories C1, C2 and C3 encrypted by the corresponding category keys KC1, KC2 and KC3.

In other examples the categories (C1, C2, . . . Cn) are user preferences, usage statistics, location, presence information, pseudo, each of these categories being encrypted by the digital data source device (SE1, SE2, . . . SEn) with a category key (KC1, KC2, . . . KCn) pertaining to the category (C1, C2, . . . Cn) of data According to an embodiment, the database (DB1, DB2, . . . DBn) is distributed at a plurality of storage locations in the open communication network (C), the storage locations may depend on the category (C1, C2, . . . Cn) of user private data (dC1, dC2, . . . dCn). For example categories corresponding to sensitive data are located in more secures location than categories of data having a low privacy level or easily reproducible if lost or corrupted. Location may also be determined for accessibility and performance purposes.

According to another embodiment, the database (DB1, DB2, . . . DBn) is partially or entirely stored in at least one remote storage device at a predetermined location in the open communication network (C).

The database controllers DBCE update at scheduled time or upon request the databases DB with the latest values produced by the digital data source devices SE1, SE2, SE3, SE4, SE5, SE6 and SE7 as well as with any changes in the user data. These update operations may be carried out automatically or manually or a combination of both by stakeholders having particular rights or authorization to send specific update commands to the database controllers DBCE.

A stakeholder S1 sends a request Rq (dC1, dC2, dC3) with a client digital data processing device CE1 to the network C. The request Rq (dC1, dC2, dC3) including at least an instruction to access to the data d of a user identified by an identifier ID Uj is forwarded to a database controller DBCE which returns a reply Rp [(dC1)KC1, (dC2)KC2, (dC3)KC3] by sending data concerning the user Uj of categories CA, C2, C3, i.e. user private data (dC1)KC1, (dC2)KC2, (dC3)KC3 each encrypted by the respective category key KC1, KC2, KC3.

The client digital data processing device CE1 of the stakeholder S1 only owns the category keys KC1 and KC3 so that only the data of categories C1 and C3 can be decrypted by the stakeholder S1, the encrypted data (dC2)KC2 remaining inaccessible as the category key KC2 is not available.

The client digital data processing device CE may consist of any server or terminal device able to connect to the open network and to receive data previously requested such as personal computer, a personal digital assistant or a smart phone.

Digital data source devices SE and client digital data processing devices CE may be located anywhere in the open network, e.g. in a smart grid or a home area network.

According to an embodiment a digital data source device SE and a client digital data processing device CE are located in a same physical device or server.

According to a further embodiment, in a home area network, the device corresponds to a network access home gateway or home energy gateway.

According to a further embodiment, the database controllers DBCE filter the request of the stakeholder in such a way to return only the category of user private data which the stakeholder can decrypt, the other categories being not sent. In this case, the configuration of the client digital data processing device CE including the available category keys KC of the stakeholder is registered into a database of the network accessible to the database controllers DBCE.

In FIG. 2, the stakeholder S2 sends a request Rq [dC2] for accessing data of a set of users and receives a reply Rp [(dC2)KC2] including only the category C2 of data dC2 that the client digital data processing device CE2 can decrypt. In fact only the category key KC2 is available to this client digital data processing device CE2.

The stakeholder S3 sends a request Rq [dC1, dC2] for the data of a set of users and receives in reply Rp [(dC1)KC1, (dC2)KC2] the data of categories C1 and C2. The client digital data processing device CE3 owns the category keys KC1 and KC2 necessary for decrypting the categories C1 and C2.

In a further embodiment, the encrypted categories of the requested user private data are accompanied by a cryptogram including the necessary category keys encrypted with a personal key of the stakeholder.

For example the stakeholder S1 receives the reply Rp [(dC1)KC1, (dC2)KC2, (dC3)KC3] with a cryptogram (KC1, KC3)KS1 where KS1 is a personal key of the stakeholder S1. In this case only the personal key KS1 is stored in the client digital data processing device CE1 since the category keys are provided by the database controllers DBCE where the stakeholder S1 may also be recorded.

The invention claimed is:

1. A method for controlling access, via an open communication network, to user private data comprising a plurality of data sets provided by a plurality of digital data source devices, said method comprising:
   dividing, by at least one database controller, the user private data into a plurality of categories, each category defining a privacy level of the user private data, each category being associated with one respective category key, each data set being assigned to one of the plurality of categories, each category key being independent of other category keys such that when protection of data associated with one category key becomes violated data associated with other category keys remains protected;
   encrypting by each digital data source device the user private data of each category with the respective category key associated with the category of the user private data, each data set only being encrypted with the one respective category key associated with the category of the data set;
   storing temporally or permanently the encrypted user private data in at least one database controlled by the at least one database controller;
   attributing to a stakeholder at least one client digital data processing device configured to access at least one category of user private data by the at least one database controller according to the categories corresponding to the category key made available to said client digital data processing device of the stakeholder; and
   authorizing, by the at least one database controller, the access to the at least one category of user private data for the at least one client digital data processing device of the stakeholder by providing the at least one client digital data processing device with the respective category key associated with the at least one category of user private data via the open communication network, wherein the user private data are metering data divided into a plurality of categories, the metering data of each category being encrypted by a smart meter with a category key pertaining to the category of the metering data, the open communication network being entirely or partly a smart grid network.

2. The method according to claim 1, wherein the database is distributed at a plurality of storage locations in the open communication network.

3. The method according to claim 1, wherein the database is partially or entirely stored in at least one remote storage device at a predetermined location in the open communication network.

4. The method according to claim 1, wherein the category keys are either of symmetrical type or asymmetrical type or of a combination of symmetrical and asymmetrical keys.

5. The method according to claim 1, wherein the category keys are used in combination with other keys such as stakeholder-related keys or user-related keys.

6. The method according to claim 1, wherein the at least one database controller includes a managing center managing the plurality of digital data source devices each sending, periodically or at scheduled time, data to the at least one database controller which feeds the database.

7. The method according to claim 6 wherein the plurality of digital data source devices include smart meters, electrical vehicles, or radio-frequency identification (RFID) devices.

8. The method according to claim 1, wherein the categories are user preferences, usage statistics, location, presence information, or a combination thereof, each of these categories being encrypted by the plurality of digital data source devices with a category key pertaining to the category of data.

9. The method according to claim 1, wherein the plurality of digital data source devices and the at least one client digital data processing device are combined in a same physical device.

10. The method according to claim 9, wherein the plurality of digital data source devices and the at least one client digital data processing device are a network access home gateway or a home energy gateway.

11. The method according to claim 1, wherein the plurality of digital data source devices or the at least one client digital data processing device is combined with at least one database controller in a same physical device.

12. A system configured to control access, via an open communication network, to user private data comprising a plurality of data sets, said system comprising:
   a plurality of digital data source devices configured to provide user private data, wherein the user private data are divided into a plurality of categories, each category defining a privacy level of the user private data, each category being associated with one respective category key, each dataset being assigned to one of the plurality of categories, each category key being independent of other category keys such that when protection of data associated with one category key becomes violated data associated with other category keys remains protected, and wherein each digital data source device is configured to encrypt the user private data of each category with the respective category key associated with the category of the user private data, each data set only being encrypted with the one respective category key associated with the category of the data set;

at least one client digital data processing device attributed to a stakeholder;

at least one database configured to store temporally or permanently the encrypted user private data; and at least one database controller configured to control the at least one database;

wherein the at least one client digital data processing device is configured to access at least one category of user private data by the at least one database controller according to the categories corresponding to the category key made available to said client digital data processing device of the stakeholder, wherein the at least one database controller is configured to authorize the stakeholder access to the at least one category of user private data by providing, to the at least one client digital data processing device, the respective category key associated with the at least one category of user private data via the open communication network, and wherein the user private data are metering data divided into a plurality of categories, the metering data of each category being encrypted by a smart meter with a category key pertaining to the category of the metering data, the open communication network being entirely or partly a smart grid network.

13. The system according to claim 12, wherein the database is distributed at a plurality of storage locations in the open communication network.

14. The system according to claim 12, wherein the database is partially or entirely stored in at least one remote storage device at a predetermined location in the open communication network.

15. The system according to claim 12, wherein the at least one database controller includes a managing center managing the plurality of digital data source devices, each digital data source device being configured to send, periodically or at scheduled time, data to the at least one database controller which feeds the database, the digital data source devices including smart meters, electrical vehicles, or radio-frequency identification (RFID) devices.

* * * * *